United States Patent [19]

Deschler et al.

[11] Patent Number: 4,705,868

[45] Date of Patent: Nov. 10, 1987

[54] PROCESS FOR THE PREPARATION OF EPOXIDIZED ORGANOSILICON COMPOUNDS

[75] Inventors: Ulrich Deschler, Hanau; Andreas Grund, Darmstadt; Guenter Prescher, Hanau, all of Fed. Rep. of Germany

[73] Assignee: Degussa Aktiengesellschaft, Frankfurt, Fed. Rep. of Germany

[21] Appl. No.: 890,448

[22] Filed: Jul. 30, 1986

[30] Foreign Application Priority Data

Aug. 5, 1985 [DE] Fed. Rep. of Germany ....... 3528006

[51] Int. Cl.[4] .................. C07D 303/02; C07F 7/02; C07F 7/08; C07F 7/18
[52] U.S. Cl. .................................................. 549/215
[58] Field of Search ........................................ 549/215

[56] References Cited

U.S. PATENT DOCUMENTS

| | | | |
|---|---|---|---|
| 2,946,701 | 7/1960 | Plueddemann | 549/215 X |
| 3,242,151 | 3/1966 | Porret | 549/215 X |
| 3,334,121 | 8/1967 | Pepe et al. | 549/215 X |
| 3,427,270 | 2/1969 | Northrup | 549/215 X |
| 3,445,483 | 5/1969 | Chaffee | 549/215 |
| 3,455,877 | 7/1969 | Plueddemann | 549/215 X |
| 4,576,999 | 3/1986 | Eckberg | 549/215 X |

*Primary Examiner*—Paul F. Shaver
*Attorney, Agent, or Firm*—Beveridge, DeGrandi & Weilacher

[57] ABSTRACT

A process for the preparation of epoxidized organosilicon compounds by reacting the corresponding unsaturated organosilicon compounds with perpropionic acid in benzene solution. The said solution can also be employed in purified form with maximum contents of hydrogen peroxide, water, or mineral acid.

13 Claims, 8 Drawing Figures

$(CH_3O)_3Si-CH_2CH_2-CH-CH_2$
            $\underset{O}{\diagdown\diagup}$

PROCESS FOR THE PREPARATION OF EPOXIDIZED ORGANOSILICON COMPOUNDS

The present invention relates to the preparation of epoxidized organosilicon compounds by direct oxidation of unsaturated organosilicon compounds.

Organosilicon compounds containing at least one epoxy group or epoxy group carrying group have been the subject of technical interest for many years. They are successfully employed as a monomer, or in combination with other monomers, in the manufacture of highly valuable materials. Furthermore, they have found use as so-called bonding agents between different materials in many fields of polymer and adhesive technology.

Several processes have been known for a long time for the preparation of the described organosilanes with epoxy groups. One such method for synthesis is, for example, the catalytic addition of silanes with at least one hydrogen atom to the C=C double bond of a monoolefinic epoxide.

Precious metals such as platinum, rhodium, ruthenium, or nickel as well are used as catalysts, whereby the separation and recycling of the catalyst results in appreciable technical effort and expenditure (West German DE-OS No. 19 37 904, East German Patent DDR-PS No. 144 413, U.S. Pat. No. 3,745,206).

An essentially different option for the preparation of the described class of compounds is a process effected in the reverse order, i.e., an unsaturated silane is prepared first and the said silane is then epoxidized. This so-called direct oxidation can be effected with the aid of organic per acids (U.S. Pat. No. 3,455,877 or West German Patent DE-PS No. 1 061 321). A solution of peracetic acid in acetic acid was usually employed for this process, but the said solution was not generally usable and, depending on the type of unsaturated silane, only results in a very slow course of reaction and in very low yields (E. P. Plueddemann, G. Fanger, J. Am. Chem. Soc., 1959, Vol. 81, p. 2632; British patent GB-PS No. 1,205,819). In addition, the use of hydrous per acids with the hydrolyzable silanes produced very high losses of yield.

The large scale application of, for example, peracetic acid (West German DE-OS No. 21 59 991) produced anxieties about the safety risk. Attempts to avoid these difficulties with use of a special system, namely the use of m-chloroperbenzoic acid in halogenated hydrocarbons, failed. The yields were unsatisfactory (British patent GB-PS No. 1,205,819). There was also the added risk of appreciable corrosion due to the use of halogenated hydrocarbons. The separation and recycling or reuse of mchlorobenzoic acid resulting from the reaction likewise caused difficulties. This problem also arose with the use of other per acids and their parent acids resulting from the reaction. Direct epoxidation with 95% hydrogen peroxide could likewise not be carried out for safety reasons (West German DE-OS No. 26 07 768).

Consequently, it followed from this development of the art that the use of a percarboxylic acid in the preparation of epoxidized organosilicon compounds was not seen as appropriate.

Accordingly, the invention has as its object the epoxidation of unsaturated organosilicon compounds with a percarboxylic acid effected in such a way that in addition to highly satisfactory yields, there are no safety risks involved and the resulting parent acids can also be recovered by technically simple processing of the reaction mixture and reused.

It has now been found that this object can be achieved by reacting the organosilicon compounds with one or more carbon to carbon double bonds with perpropionic acid in benzene solution at a molar ratio of 1:1 to 1:2 (double bond to be epoxidized to perpropionic acid) at a temperature of 10° to 120° C., preferably of 40° to 70° C. Suitable organosilicon compounds containing one or several carbon to carbon double bonds are those compounds in which the carbon to carbon double bond is part of a substituent attached to the Si atom via at least one carbon atom or via a C-O bond or a C-N bond. These include, for example, silanes of the following formula, which can also be present as an isomer mixture:

Si(O—CH$_2$—CH=CH$_2$)$_4$     1

2

3

4

(CH$_3$O)$_3$Si—CH$_2$—CH$_2$—CH=CH$_2$     5

6

R = Alkyl, Aryl (C$_1$-C$_6$)

Details on the preparation of unsaturated silanes are found in the following literature:

E. P Plueddemann in Kirk-Othmer, Vol. 20, pp. 962ff.; B. E. Cooper, Process Biochemistry, 1980, pp. 9ff; Charles A. Roth, I and EC Product Research and Development, Vol. 11, 1972, p. 134.

Perpropionic acid can be prepared, for example, according to a process disclosed in West German Patent DE-PS No. 25 19 289 by reacting aqueous hydrogen peroxide with propionic acid in the presence of sulfuric acid, then extracting the resulting perpropionic acid with benzene from the reaction mixture. The perpropionic acid in benzene solution obtained thereby can be purified still further to reduce the residual content of sulfuric acid, water, and hydrogen peroxide (cf. West German Patent DE-PS No. 25 19 290). However, a perpropionic solution is preferred that requires no further purification; in other words, the crude extract from the preparation of perpropionic acid can be used directly as such. This results in a considerably reduced technical expenditure.

Therefore, a perpropionic acid solution in benzene can be used that contains up to 1.5 weight percent of hydrogen peroxide, 1.5 weight percent of water, and up to 800 ppm of mineral acid. The per acid content of the solution can vary from 10 to 30 weight percent, 20 weight percent being preferred.

The novel process can be run at various pressures; in general, standard pressure is used, but the process can also be run at excess or subatmospheric pressure.

The reaction can be run both as a batch process or as a continuous process in reactors suitable for this type of reaction. Typical reactors include agitated kettles, agitated kettle cascades, and tubular or loop-type type reactors, whereby the heat of the reaction can be removed in any manner, e.g., by evaporative cooling or by internal or external cooling equipment.

Glass, special steel, or enameled material are suitable fabrication materials for the reactors for carrying out the process embodying the invention.

The perpropionic acid is combined with the olefin or the solution thereof in a suitable solvent in any way desired. For example, both reactants can be introduced into the reactor together or in succession in any order of sequence. In a batch operating mode, the olefin is preferably introduced first and the per acid is metered in while the reaction temperature is monitored. However, the reaction can also be performed in reverse order, i.e., the per acid is charged first and the olefin is metered in with temperature monitoring. If the reaction is run continuously, both reactants can be fed into the reator separately or together. If several series connected reactors are used, such as, for example, an agitated kettle cascade or a series of agitated kettles with a tubular reactor as the subsequent reactor, the addition of both the per acid and the silane can be distributed over several reactors. Although benzene is the preferred solvent, toluene, chlorobenzene, or halogenated aliphatics such as methylene chloride, chloroform and carbon tetrachloride can be used also to dissolve the silane.

No catalyst is required for the process of the present invention.

According to the process of the invention, a continuous mode of operation is very advantageous. Pursuant to this mode, the unsaturated organosilane is charged with a solution of perpropionic acid in benzene at a molar ratio of 1:1 to 1:2 (double bond to be epoxidized to the per acid) to a reactor system, which comprises a series of 1 to 4 ideally mixed reactors and a subsequent reactor. The reaction is carried out at a temperature which is controlled within the range of 10° to 120° C. The residence time is also controlled and adjusted so that the conversion, based on the olefin double bonds used, is at least 80 mole percent downstream of the ideally mixed reactor(s) and at least 95, preferably over 98, mole percent downstream of the subsequent reactor. The reaction mixture leaving the subsequent reactor is liberated in a combination or distillation and desorption steps from benzene, propionic acid, small amounts of perpropionic acid, and other light boiling substances. The separation of the reaction mixture can be carried out according to one of the embodiments described hereinafter.

The invention is further described and illustrated by the drawings wherein.

Embodiment 1 (Batch Process)

According to this embodiment, the individual components of the reaction mixture are removed in the order of their respective boiling points, individually or as a mixture by distillation or by distillation and desorption. In this process, the fractions of benzene, residues of perpropionic acid, propionic acid, and other readily volatile components are easily removed. The epoxide remains as the bottoms. If desired, the separated benzene and the propionic acid can be returned to the per acid synthesis after additional purification steps.

Figure 1:
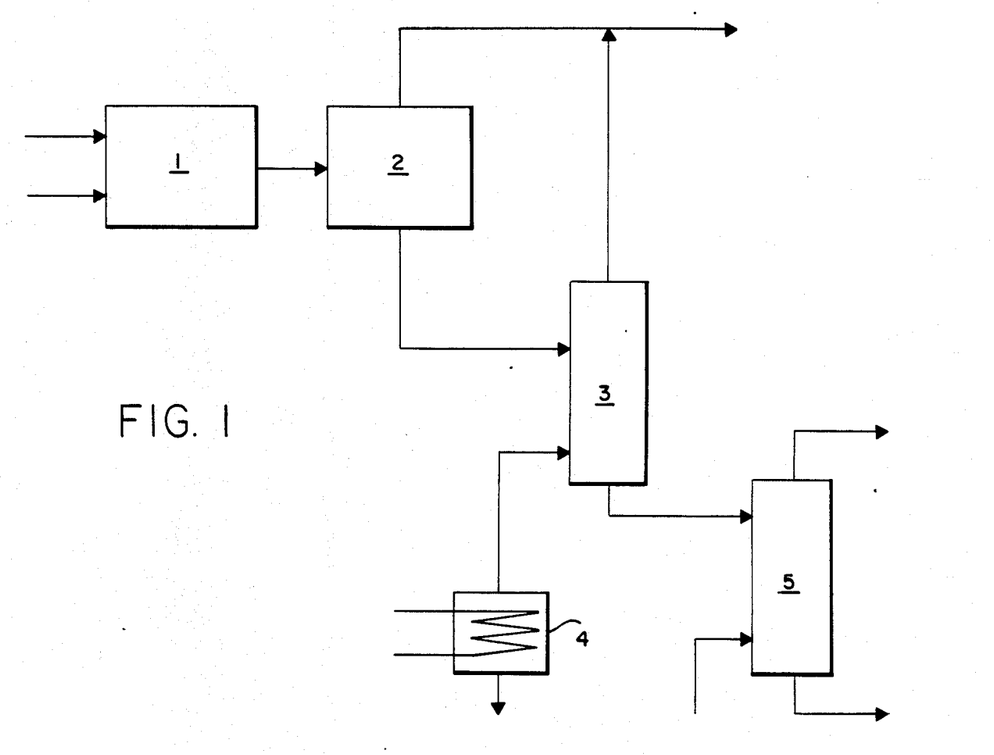
FIG. 1 is a flow chart of the process of the invention.

Embodiment 2 (Continuous Process, FIG. 1)

According to this continuous variant of the process and as illustrated in FIG. 1, after the reaction mixture has left reaction unit 1, most of the benzene, propionic acid, and unreacted perpropionic acid are first removed in the one- or multistage distillation unit 2. Suitable for distillation devices are thin film, falling film, or circulation evaporators. Advantageously, distillation is effected at a reduced pressure of 0.5 to 600, preferably 10 to 300, mbar (temperature of the heating medium is 50° to 150° C.). Average residence times, based on the individual evaporation stages, are a maximum of 10 minutes, residence times of a maximum of 5 minutes being preferred.

Figure 3:
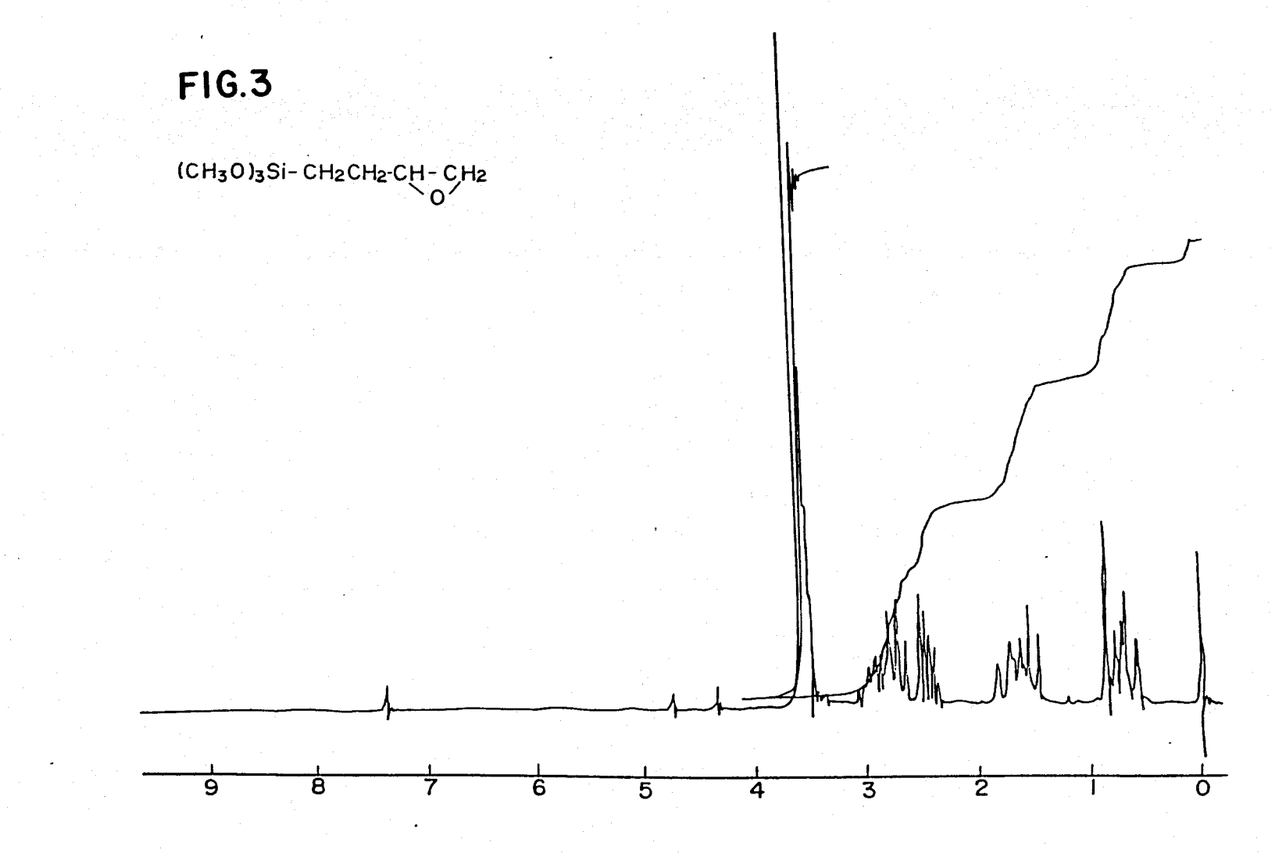
FIG. 3 is an H-NMR spectra of the crude product of Example 1.
Figure 4:
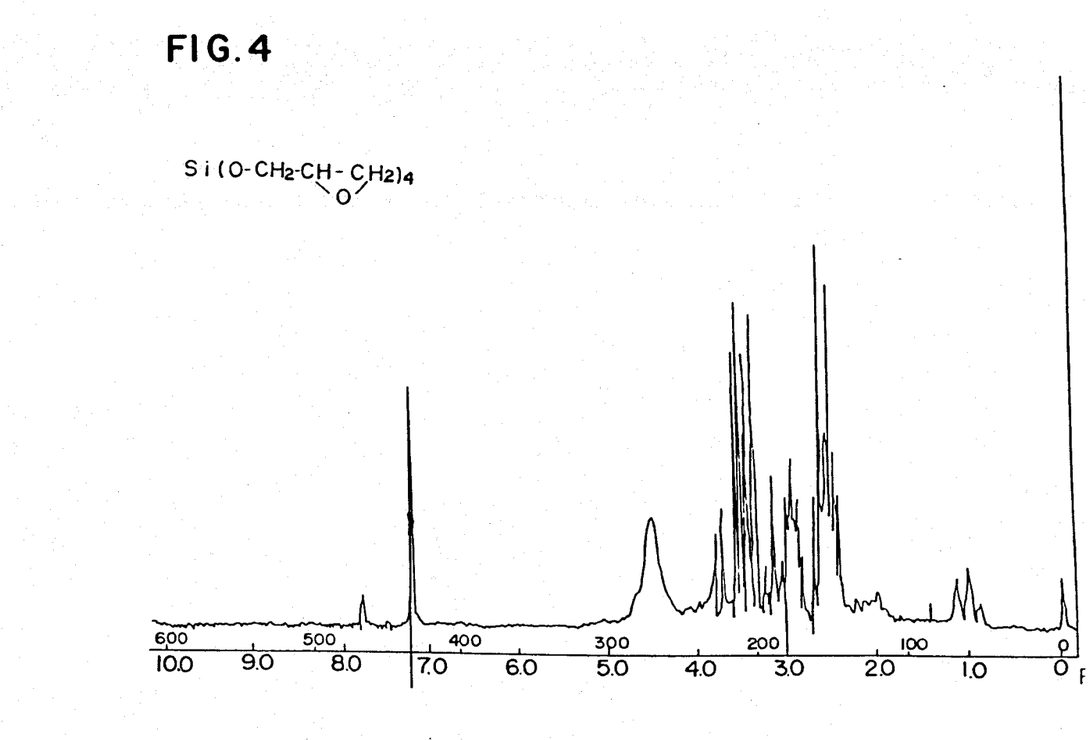
FIG. 4 is an H-NMR spectra of the crude product of Example 2.
Figure 5:
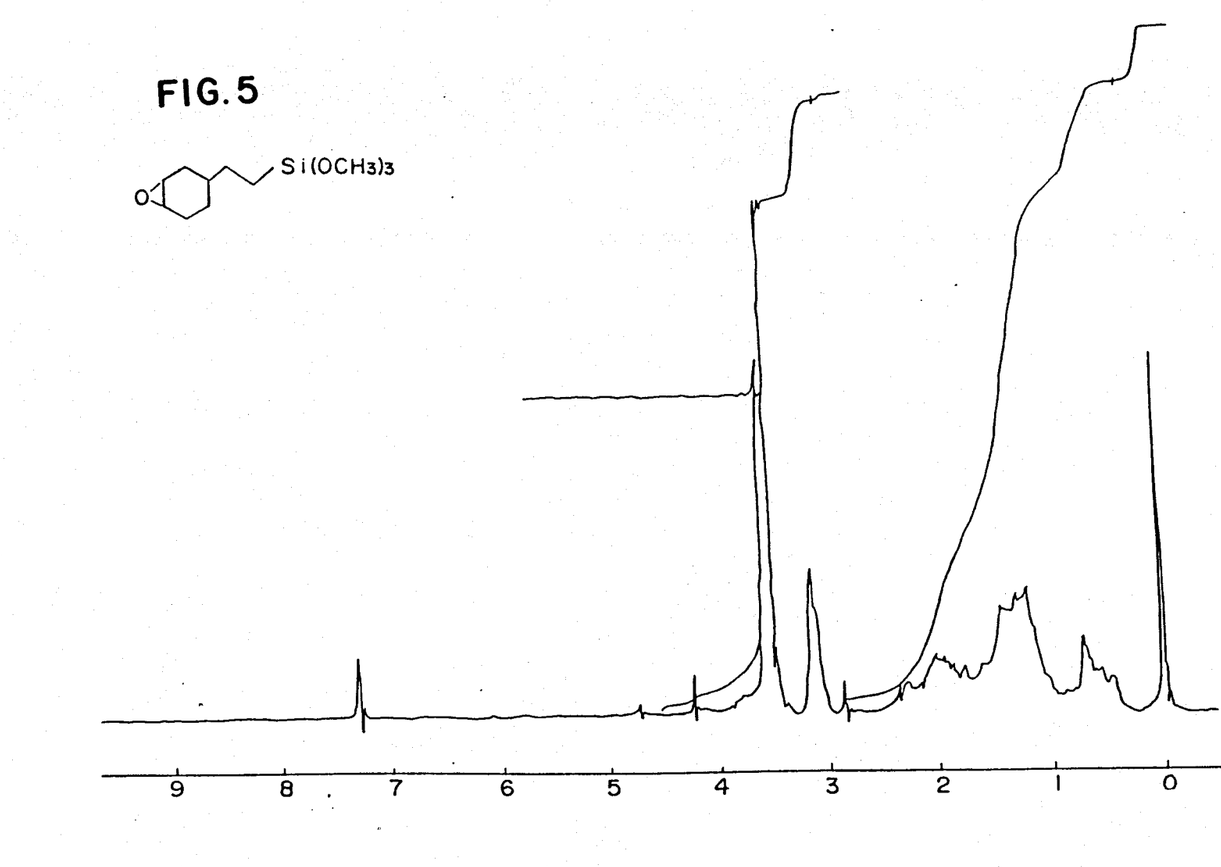
FIG. 5 is an H-NMR spectra of the crude product of Example 3.
Figure 6:
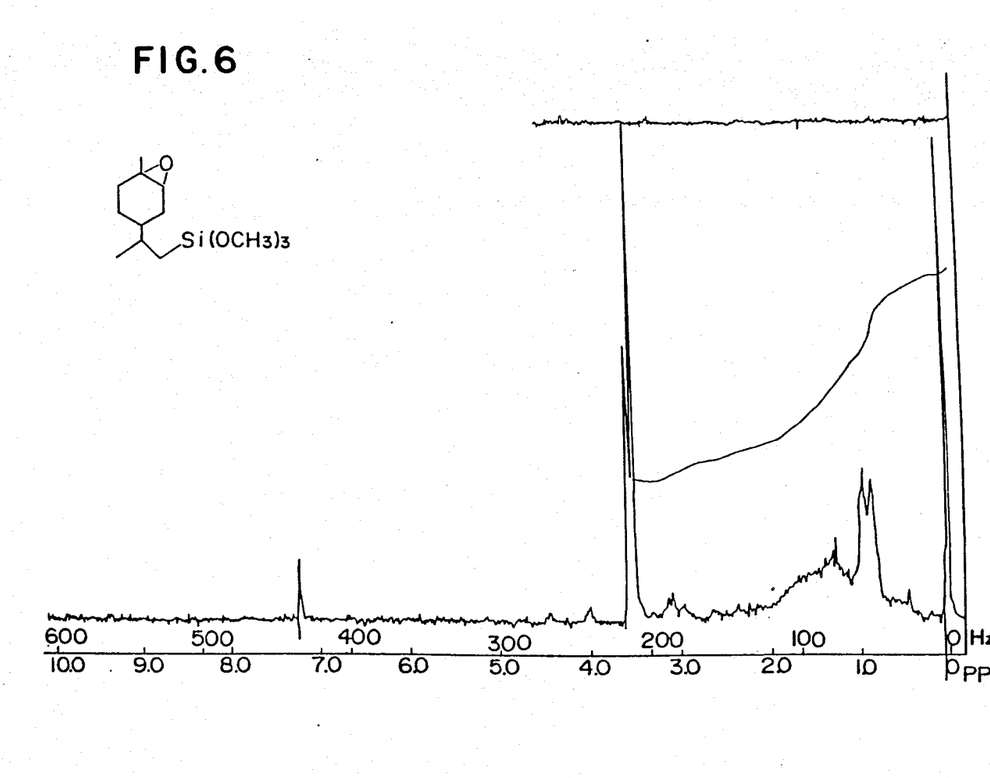
FIG. 6 is an H-NMR spectra of the crude product of Example 4.
Figure 7:
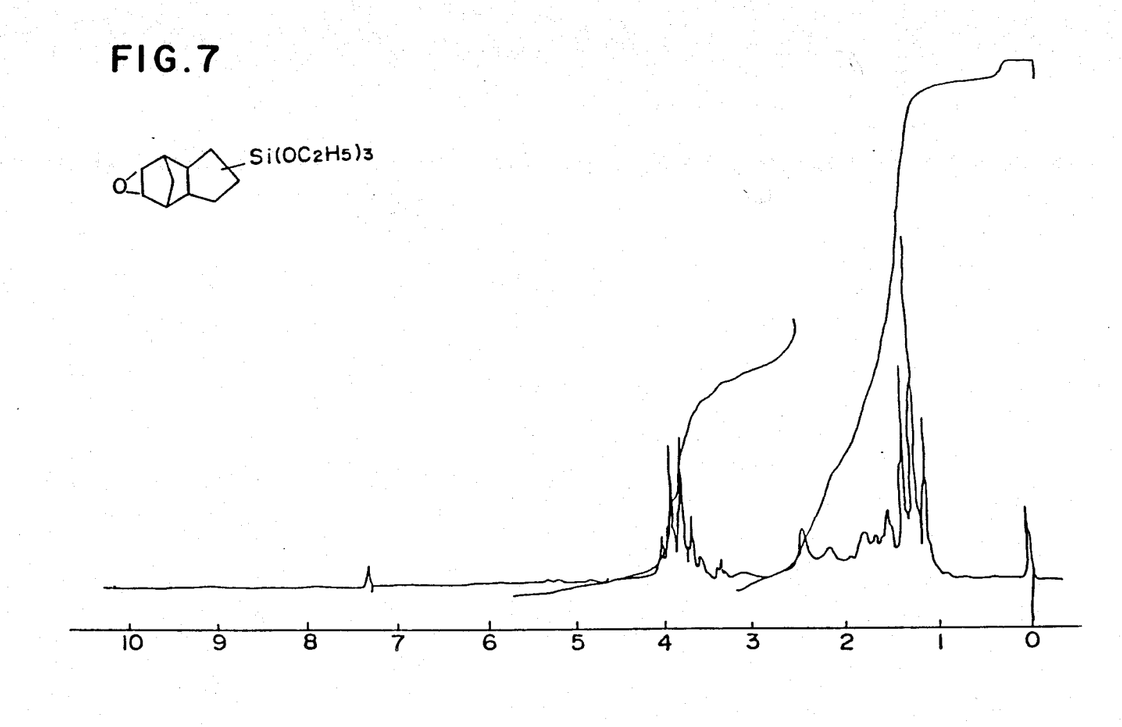
FIG. 7 is an H-NMR spectra of the crude product of Example 5.
Figure 8:
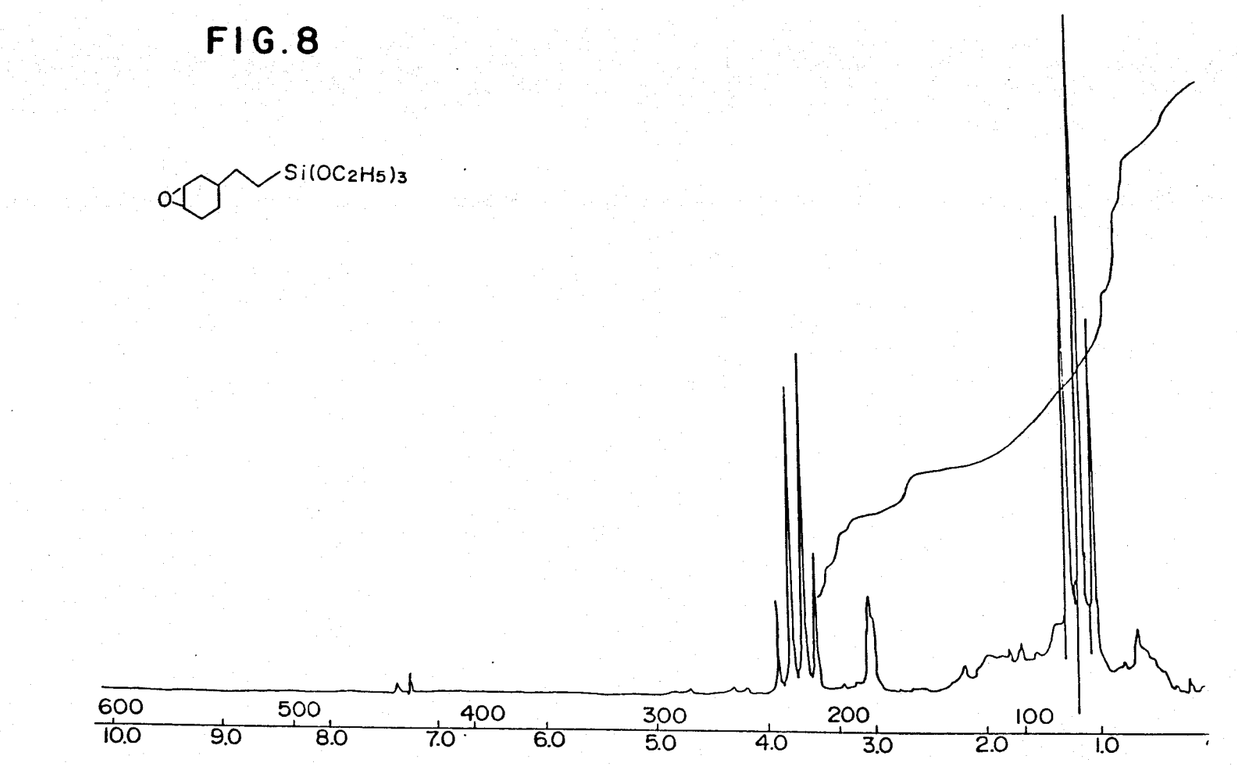
FIG. 8 is an H-NMR spectra of the crude product of Example 6.

According to the process of the invention, any amount of propionic acid remaining in the crude product is then removed by desorption in desorption unit 3 with benzene vapor that is generated in evaporator 4. The vapors from desorption unit 3 can either be past distillation unit 2 or be passed therethrough. After this step, any remaining traces of benzene are desorbed from the epoxide with steam from evaporator 6 in desorption unit 5 and/or with nitrogen or other inert gases in desorption unit 8. It is especially preferred to desorb first with steam, then with inert gases. The condensate from desorption unit 5 separates in phase separator 7 into an organic phase and water. The water is returned to evaporator 6, after enrichment, if necessary. The organic phase, which contains mostly benzene and propionic acid, is returned to perpropionic acid synthesis or to epoxidation after further processing, if necessary. Likewise, the streams of condensate consisting primarily of benzene and unreacted perpropionic and propionic acids and originating from distillation of desorption units 2 and 3, are returned, after further separation - cf. FIG. 3 - which will be described below; to per acid synthesis or to epoxidation.

In all examples, devices such as, for example, the falling film evaporator, Sambay evaporator, columns with built in packing or fill packing material, or similar means that enable proper mass transfer between gaseous and liquid states and are known to those skilled in the art are suitable as the desorption unit.

Figure 2:
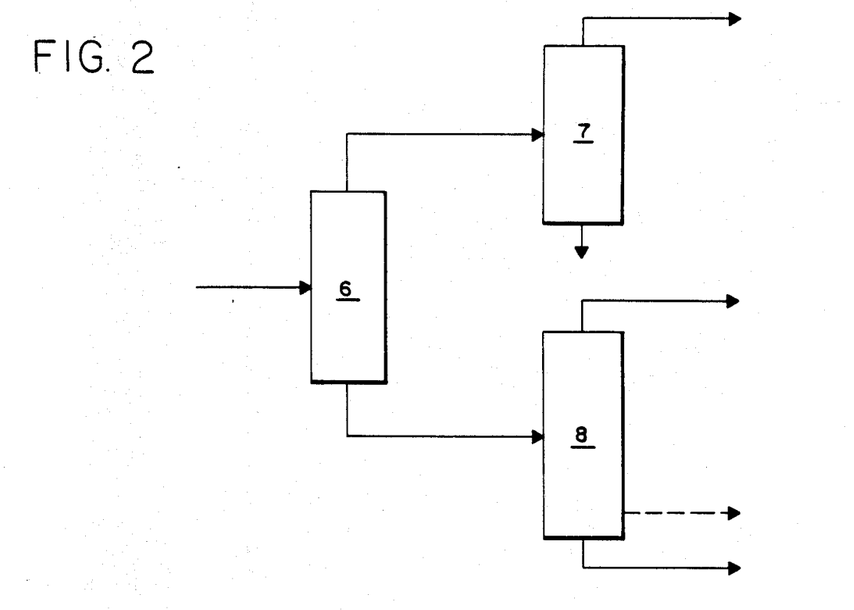
FIG. 2 is a flow chart of the distillation system of the invention.

In all embodiments of the invention, condensates are obtained whith are composed mainly of benzene, unreacted perpropionic acid, and other light boiling substances. According to the process of the invention, then condensates are transferred to distillation unit 6 which includes one or more columns (FIG. 2). This unit produces benzene as the overhead and in some cases other light boiling substances. In certain cases, the former is returned, after further distillation, to unit 7 for the preparation of perpropionic acid. A mixture of propionic acid, perpropionic acid, and benzene with a benzene proportion of 5 to 35 weight percent based on the bottoms mixture, accumulates in the bottom of distillation unit 6. This mixture is fed to another distillation unit 8, in which the total amount of added benzene and perpropionic acid with portions of propionic acid is drawn off at the top and, in so doing, a concentration of perpropionic acid in the distillate of 25 weight percent is not exceeded. This overhead is returned to the process of preparing perpropionic acid or to the reaction of the olefin with perpropionic acid. There is obtained as bottoms in column 8 propionic acid, which, after further processing such as by high purity distillation, is recycled to the preparation of perpropionic acid, after supplementing if necessary. It is of particular advantage to draw off the propionic acid obtained in unit 8 as a vapor above the bottom and to condense it, thereby dispensing with one more purification step.

According to the invention, all distillation processing steps are preferably carried out at reduced pressure, e.g., 0.5 to 600 mbar. Columns in which benzene or propionic acid is obtained as overhead can likewise be run at standard pressure.

The novel process offers a series of surprising advantages. According to this process, it is possible via the so-called Prileschajew reaction to produce the abovementioned diepoxide on a commercial scale safely and with high yields. The product thus obtained is distinguished by its exceptional purity, high epoxide content, low viscosity, lack of odor, and light color.

The content of ionic contaminants ($Na^+$, $Cl^-$, $Fe^{3+}$, etc.) is also very low, or not detectable, as a result of which a product becomes available with clearly better properties than epoxysilanes produced by other processes. Particularly for applications in the field of microelectronics, quality requirements are set forth the purity of the products to be employed there, which can very easily be met by the process advocated by the invention.

The process described herein is economical, since all auxiliary agents are recycled. The process is by no means harmful to the environment, because only water is the waste product from the oxidation agent. Moreover, only small amounts of other light boiling substances, and distillation residues are obtained, which can be disposed of safely and without serious problems.

According to the invention, only short reaction times are necessary, which makes the commercial operation highly cost effective.

It is surprising and unforeseeable that the reaction of the abovementioned silanes with a crude perpropionic acid, which still contains mineral acid, water, and hydrogen peroxide in the concentrations mentioned above, can be carried out, and that side and secondary reactions are suppressed to the highest degree possible. Furthermore, it was unforeseeable that the reaction mixture thus obtained can be processed according to the invention by distillation or by distillation and desorption, without markedly reducing the epoxide content of the product.

The invention is further illustrated and described in the following examples.

EXAMPLE 1 (BATCH)

104 g (0.25 moles) of perpropionic acid (22 weight percent) in benzene was added to 40.0 g (0.23 moles) of 4-trimethyoxysilyl-1-butene with stirring at 75° C. over a 2 hour period. The perpropionic acid was prepared according to West German Patent DE-PS No. 25 19 289 and contained 0.59 weight percent of hydrogen peroxide, 0.91 weight percent of water, and 620 ppm of sulfuric acid, and was also used in all subsequent tests. Stirring was continued for 2 hours at 75° C. after the addition. The olefin conversion at this point was 98%. The clear, pale yellow solution thus obtained was passed through a thin film evaporator over a 20 minute period at 90° C. and a pressure of 100 mbar, during which about 180 g/hour of benzene vapor was introduced countercurrently at the same time. The crude epoxide thus obtained was then passed through the thin film evaporator at 90° C./30 mbar; a weak nitrogen stream was passed countercurrently. 38 g of 1,2-epoxy-4-trimethoxysilylbutane with an epoxy content of 88% (titr.) was obtained as the bottoms. Further purification was effected by distillation in vacuum (boiling point 90° C./12 mbar).

Elemental analysis:

|  | C | H |
|---|---|---|
| Calculated: | 43.72 | 8.39 |
| Found: | 43.20 | 8.43 |

EXAMPLE 2 (BATCH)

0.57 moles of perpropionic acid (22 weight percent) in benzene were added to 33.0 g (0.13 moles) of tetra-(1-propenoxy)silane with stirring at 70° C. over a 1 hour period. Stirring was continued for 3 hours at 75° C. The olefin conversion at this point was 90.2%. Following the procedures as in Example 1 produced 36.3 g of tetraglycidylsilane as the crude product with an epoxide content of 88.1% (titr.).

Elemental analysis:

|  | C | H |
|---|---|---|
| Calculated: | 45.00 | 6.29 |
| Found: | 44.66 | 6.04 |

EXAMPLE 3 (BATCH)

0.39 moles of perpropionic acid (22 weight %) in benzene was added to 80 g (0.35 moles) of 1-trimethoxysilylethyl-cycylohexene-3 with stirring and cooling to 40° C. over a 2 hour period. After 2 hours of continued reaction at 50° C., the olefin conversion was 94.4%. Following the procedures as in Example 1 produced 75 g of crude trimethoxysilylethyl-epoxy-cyclohexene with an epoxide content of 84% (GC).

Elemental analysis:

|  | C | H |
|---|---|---|
| Calculated: | 53.63 | 9.00 |
| Found: | 53.29 | 9.04 |

EXAMPLE 4 (BATCH)

0.15 moles of perpropionic acid (22 weight %) in benzene were added to 36.2 g (0.14 moles) of trimethoxysilyllimonene (isomer mixture) with stirring and cooling to 40° C. over a 40 minute period. After 2.5 hours of continued reaction at 50° C., the olefin conversion was 98.6%. Following the procedures as in Example 1 produced 33.2 g of epoxidized trimethoxysilyllimonene with an epoxide content of 88.3% (GC) as the crude product.

Elemental analysis:

|  | C | H |
|---|---|---|
| Calculated: | 56.90 | 9.55 |
| Found: | 56.26 | 10.02 |

EXAMPLE 5 (CONTINUOUS)

1.32 moles of perpropionic acid in benzene (22 weight %) and 1.2 moles of triethoxysilyldicyclopentadiene (isomer mixture) (which corresponds to a molar ratio of per acid to olefin of 1.1:1) were charged hourly to the first agitated kettle of a reaction unit consisting of two agitated kettles with volumes of 1000 ml and 1200 ml, respectively, and a subsequent reactor designed as a tubular reactor with a volume of 790 ml. The reaction temperature in reactor 1 was 40° C., in reactor 2 it was 40° C., and in the subsequent reactor it was 50° C. Conversions of olefin were 92% downstream of the agitated kettle cascade, and 96.1% downstream of the tubular reactor. According to Process Embodiment 2, benzene, perpropionic acid, the propionic acid were separated first in a Sambay evaporator with a surface area of 0.065 m² at 90° C./100 mbar. The residual propionic acid was desorbed in a second evaporator of the same type and same surface area at 90° C./100 mbar at a flow rate of 320 g/hour of benzene vapor, whereby all vapors from this evaporator were passed through evaporator 1 countercurrently to the product stream. Subsequently, the epoxide was treated in a desorption unit consisting of a Sambay evaporator (surface area of 0.065 m²) at 95° C./30 mbar with 14 g/hour of nitrogen. 362.1 g of epoxidized triethoxysilyldicyclopentadiene as an isomer mixture was obtained hourly as product.

Elemental analysis:

|  | C | H |
|---|---|---|
| Calculated: | 61.50 | 9.03 |
| Found: | 61.32 | 9.26 |

EXAMPLE 6 (CONTINUOUS)

1.2 moles of perpropionic acid in benzene (22 weight %) and 1.1 moles of triethoxysilylethylcyclohexene3 (which corresponds to a molar ratio of per acid to olefin of 1.09:1) were charged hourly to the first agitated kettle of a reaction unit consisting of two agitated kettles each with a volume of 1500 ml and a subsequent reactor designed as a tubular reactor with a volume of 790 ml. The reaction temperature in reactor 1 was 41° C., in reactor 2 it was 40° C., and in the subsequent reactor it was 50° C. Conversions of olefin were 93.4% downstream of the agitated kettle cascade, and 96.3% downstream of the tubular reactor. The procedure followed Example 5, during which, however, all vapors from evaporator 2 were conducted passed evaporator 1. After desorption with nitrogen as in Example 5, 306.8 g of epoxide with a content of 91.4% (titr.) was obtained.

Elemental analysis:

|  | C | H |
|---|---|---|
| Calculated: | 58.29 | 9.78 |
| Found: | 57.86 | 9.55 |

Variations and modifications of the foregoing will be apparent to those skilled in the art and are intended to be encompassed by the claims appended hereto.

We claim:

1. A process for the preparation of epoxidized organosilicon compounds comprising reacting an organosilicon compounds with one or more carbon to carbon double bonds with perpropionic acid in a benzene solution at a molar ration 1:1 to 1:2 (double bond to be epoxidized to perpropionic acid) at a temperature of 10° to 120° C.

2. The process according to claim 1, wherein the temperature is 40° to 70° C.

3. The process according to claim 1, wherein the carbon to carbon double bond is part of a substituent which is attached to the silicon atom via at least one carbon atom or via a C-O bond or a C-N bond.

4. The process according to claim 1, wherein and organosilicon compound with at least one hydrolyzable group is used.

5. The process according to claim 1, wherein a perpropionic acid solution is used that has a maximum content of 1.5 weight percent of hydrogen peroxide, 1.5 weight percent of water and 800 ppm of mineral acid.

6. A process according to claim 1, further comprising continuously charging the unsaturated organosilane with a solution of perpropionic acid in benzene at a molar ratio of 1:1 to 1:2 to a reaction system comprising a series of 1 to 4 ideally mixed reactors and a subsequent reactor, controlling the temperature between 10° to 120° C., controlling the residence time of the reaction mixture so that the conversion, referred to the olefin double bonds used, is at least 80 mole percent downstream of the ideally mixed reactor(s) and at least 95 mole percent downstream of the subsequent reactor.

7. The process according to claim 6, further comprising recovering benzene, propinonic acid, and small amounts of perpropionic acid from the mixture emerging from the subsequent reactor by distillation and subsequently desorption.

8. The process according to claim 7, wherein the distillation and desorption steps are carried out at reduced pressure of 10 to 300 mbar at temperatures of the heating medium of 50° to 150° C. and with residence times of a maximum of 10 minutes in the separate steps.

9. The process according to claim 6, wherein initially benzene and propionic acid, as well as perpropionic acid, are removed by distillation, whereupon any remaining amount of propionic acid in the crude epoxide is further removed by desorption with benzene vapor and the benzene and traces of propionic acid are driven off immediately thereafter by desorption with inert gases.

10. The process according to claim 7, wherein a mixture is obtained from the combination of distillation and desorption steps and comprises benzene, propionic acid, and perpropionic acid, conduction said mixture to a distillation unit including two or more distillation columns, and removing benzene, in a mixture with other low boiling substances, at the top in the first distillation step and returning benzene to the process for preparing perpropionic acid, as well as the portions of benzene at the bottom in amounts 5 to 35 weight percent based on the bottoms mixture, and passing the said mixture to a second distillation step removing the total amount of the benzene and perpropionic acid contained therein with the portions of propionic acid at the top, and in so doing a concentration of perpropionic acid in the overhead product of more than 25 weight percent is not exceeded, returning said overhead product to the process for preparing perpropionic acid or to the reaction of perpropionic acid with olefin, drawing off the propionic acid as bottoms, if necessary in the vapor state, and returning it to the process of preparing perpropionic acid.

11. An isomer mixture of epoxysilanes of the formulas:

A

B

C

D in which x is 1 or 2 and R represents a $C_1$–$C_6$ alkyl or aryl.

12. The process according to claim 6, wherein the conversion referred to the olefin double bonds used is at least over 98 mole percent downstream of the subsequent reactor.

13. The process according to claim 8, wherein the residence time is a maximum of 5 minutes.

* * * * *